United States Patent [19]

Harvey et al.

[11] 4,430,381
[45] Feb. 7, 1984

[54] MONOCARBOXYLIC ACID ANTIMICROBIALS IN FABRICS

[75] Inventors: Susan L. Harvey; James L. Cresswell; B. Jerry L. Huff, all of Memphis, Tenn.

[73] Assignee: The Buckeye Cellulose Corporation, Cincinnati, Ohio

[21] Appl. No.: 392,193

[22] Filed: Jun. 25, 1982

[51] Int. Cl.³ .................... B32B 23/00; B05D 3/02
[52] U.S. Cl. ..................... 428/284; 106/15.05; 427/389.9; 427/392; 427/393.4; 427/412; 428/286
[58] Field of Search .......... 427/412, 411, 389.9, 427/393.4, 392; 106/15.05, 286.7, 2, 33, 36; 428/284, 274, 248, 321, 245, 249, 246, 286; 424/153, 78, 26

[56] References Cited

U.S. PATENT DOCUMENTS

| | | | |
|---|---|---|---|
| 1,772,975 | 8/1930 | Wieland. | |
| 2,154,449 | 4/1939 | Hoffman et al. | 99/90 |
| 2,190,714 | 2/1940 | Hoffman et al. | 99/224 |
| 2,466,663 | 4/1949 | Russ et al. | 167/58 |
| 2,536,983 | 1/1951 | Owen | 167/30 |
| 2,729,586 | 1/1956 | Peck | 424/177 |
| 2,837,462 | 6/1958 | Morin | 167/84 |
| 2,883,322 | 4/1959 | Whipple | 167/39 |
| 3,034,957 | 5/1962 | Smith et al. | 424/27 |
| 3,061,469 | 10/1962 | Manowitz et al. | 117/138.5 |
| 3,072,534 | 1/1963 | Roth et al. | 167/84 |
| 3,152,957 | 10/1964 | Sakuma et al. | 167/84 |
| 3,255,222 | 6/1966 | Horowitz | 260/414 |
| 3,404,987 | 10/1968 | Kooistra et al. | 99/150 |
| 3,579,628 | 5/1971 | Gander et al. | 424/28 |
| 3,728,213 | 4/1973 | Hinz | 162/161 |
| 3,867,300 | 2/1975 | Karabinos et al. | 252/106 |
| 4,002,775 | 1/1977 | Kabara | 426/532 |
| 4,008,351 | 2/1977 | Inoue et al. | 428/411 |
| 4,053,670 | 10/1977 | Le Poutre | 428/156 |
| 4,172,841 | 10/1979 | Danna et al. | 106/15.05 X |
| 4,259,383 | 3/1981 | Eggensperger et al. | 428/72 |
| 4,343,788 | 8/1982 | Mustacich et al. | 424/78 |

FOREIGN PATENT DOCUMENTS

| | | | |
|---|---|---|---|
| 553057 | 2/1958 | Canada. | |
| 1098039 | 3/1981 | Canada | 167/263 |

OTHER PUBLICATIONS

European Patents Application No. 0,022,289, Mustacich et al., dated 1/14/81.
No. 9820, Merk Index,, 9th Ed. (1977), p. 1309.

*Primary Examiner*—Thurman K. Page
*Attorney, Agent, or Firm*—Milton B. Graff, IV; John V. Gorman; Richard C. Witte

[57] ABSTRACT

A process for imparting antimicrobial properties to a material comprises applying to the material an external binder system having dissolved therein a salt of a monocarboxylate antimicrobial agent, and then applying to the material a water-proofing treatment having dissolved therein a substantially nonantimicrobial proton donor.

17 Claims, No Drawings

MONOCARBOXYLIC ACID ANTIMICROBIALS IN FABRICS

TECHNICAL FIELD

This invention relates to materials in which monocarboxylic acid antimicrobials are incorporated and processes for incorporating such antimicrobials in the materials.

BACKGROUND OF THE INVENTION

The incorporation of antimicrobial substances in fabrics, paper, and related materials to prevent microbial growth and contamination in the material is well known. U.S. Pat. No. 3,728,213 issued to Charles F. Hinz on Apr. 17, 1973, discloses the incorporation of pseudoureas as antimicrobials in nonwoven fabrics utilized as surgical drapes, hospital gowns, etc.

Antimicrobials that are incorporated into fabrics which are activated when the fabrics are wetted are also known in the art. U.S. Pat. No. 2,883,322 issued to Francis O. Whippel on Apr. 21, 1959, discloses a cellulosic paper laminate with one layer containing an ammonium salt and another layer in contact with the first containing an alkaline compound. When wetted, the ammonium salt and alkaline compound react to form ammonia which acts as an antimicrobial. U.S. Pat. No. 3,152,957 issued to Akira Sakuma et al. on Oct. 13, 1964, also discloses a system in which an antimicrobial precursor is kept in one layer and a base which will activate the antimicrobial precursor is kept in a second layer in contact with the first such that when both are wetted, the antimicrobial will be liberated. U.S. Pat. No. 3,579,628 issued to Robert J. Gander et al. on May 18, 1971, discloses antimicrobial precursors that are incorporated in fabrics which when contacted with water react with the water to form formaldehyde which acts as an antimicrobial.

The use of carboxylates either alone or in conjunction with other substances to inhibit the growth of bacteria, fungi and molds in a variety of products is well known. For example, sodium propionate is routinely added to commercial bread to inhibit mold. The Merck Index, Seventh Edition, page 1117, teaches that zinc propionate is used as a fungicide on adhesive tape to reduce plaster irritation caused by molds, fungi and bacteria action.

U.S. Pat. No. 1,772,975 issued to Herman Wieland on Aug. 12, 1930, teaches the use of solutions of lactic acid, acetic acid, or homologues thereof, as antiseptics at properly adjusted pH's. U.S. Pat. No. 2,466,663 issued to Walter R. Russ et al. on Apr. 5, 1949, describes the use of caprylic (octanoic) acid to combat mycotic infection or growths. This substance may be formulated to be used topically as a liquid, ointment or butter in the treatment of surface infections. Russ also discloses that salts of caprylic acid including sodium caprylate may be used in his antifungal products; he prefers that they have a pH between 4.5 and 10.5. U.S. Pat. No. 2,190,714 issued to Charles Hoffman et al. on Feb. 20, 1940, claims a method of inhibiting mold growth in food products other than margarine and sourdough bread by adding a $C_3$-$C_{12}$ saturated branched or straight chain monocarboxylic aliphatic acid thereto.

U.S. Pat. No. 4,002,775 issued to Jon J. Kabara on January 11, 1977, describes fatty acids and derivatives as antimicrobial agents. According to Kabara, caprylic (octanoic) acid is not inhibitory to any of the microorganisms under the test conditions. However, properly used in the manner disclosed herein, octanoic acid has been found to be a particularly potent antimicrobial agent when incorporated into nonwoven fabrics.

U.S. Pat. No. 2,154,449 issued to Charles Hoffman et al. on April 18, 1939, describes the use of $C_3$-$C_{12}$ saturated branched or straight chain monocarboxylic aliphatic acids or their salts as mold inhibitors to protect a variety of materials susceptible to mold including foods, tobacco, paper, leather, textiles, etc. U.S. Pat. No. 2,729,586 issued to Samuel M. Peck on Jan. 3, 1956, discloses that $C_3$-$C_{11}$ monocarboxylic acids are bacteriostatic as well as fungistatic. Peck recognizes that many of the monocarboxylic acids have an unpleasant odor and are consequently unsuitable for use in some applications. Peck discloses the use of chlorophyll in combination with monocarboxylic acids to provide an antimicrobial in wet dressings which has an improved odor.

Canadian Pat. No. 553,057 issued to Henry J. Ferlin et al. on Feb. 11, 1958, discloses that $C_9$-$C_{12}$ saturated aliphatic monocarboxylic acids are powerful bactericides in aqueous solution at a pH below 6 but are much less effective at higher pH's.

Canadian Pat. No. 1,098,039 issued to Roger L. Stone on Mar. 24, 1981 describes intravenous aqueous solutions incorporating $C_4$-$C_9$ n-fatty acid antimicrobials. It is the equivalent of U.S. Application Ser. No. 816,625, filed July 18, 1977, now abandoned, which is a continuation-in-part of Application Ser. No. 709,342, filed July 28, 1976, now abandoned. Co-pending Application Ser. No. 918,532 which is a continuation-in-part of U.S. Application Ser. No. 816,625, is incorporated herein by reference.

Co-pending Application Ser. No. 53,619 of Robert V. Mustacich et al., filed June 29, 1979, which is incorporated herein by reference, discloses carboxylate antimicrobial agents releasably incorporated within a polymer matrix, said polymer also containing a substantially nonantimicrobial proton donor. An equivalent to this application was published as European Patent Office Application No. 0022289 on Jan. 14, 1981.

It is an object of the present invention to incorporate monocarboxylate antimicrobial precursors into nonwoven fabrics and the like such that they exhibit antimicrobial activity upon being wetted.

It is a further object of this invention to produce such antimicrobial treated materials with minimal unpleasant odor.

These and other objects will become apparent from the following detailed description. All percentages herein are by weight unless otherwise specified.

SUMMARY OF THE INVENTION

The invention described herein is a process for imparting antimicrobial properties to materials. A salt of a monocarboxylate antimicrobial agent is incorporated into an external binder system which is applied to the material. A substantially nonantimicrobial proton donor is applied to the material in a separate step with a waterproofing treatment.

DETAILED DESCRIPTION OF THE INVENTION

A variety of materials such as woven fabrics, nonwoven fabrics, papers, etc., can be treated by the process of the present invention in order to impart antimicrobial activity to them. The materials are preferably flexible and must be at least somewhat absorbent before treatment according to the process of the present invention. The preferred material for use in the present invention is the class of materials known as nonwoven fabrics, especially those comprising cellulosic fibers. Of particular use in the present invention are nonwoven fabric laminates having at least one cellulosic ply. An example of nonwoven fabric laminates for which the present invention can be utilized are those described in U.S. Pat. No. 4,113,911 issued to Larry L. LaFitte et al., on Sept. 12, 1978, the disclosure of which is hereby incorporated by reference. The present invention is especially useful for providing nonwoven fabrics with antimicrobial properties when such fabrics are to be utilized for hospital or surgical purposes and control of microbial growth or contamination is required.

When a nonwoven fabric laminate such as that of LaFitte is to be used as a surgical fabric, it is preferably treated in order to reduce fiber linting from the surface of the fabric and also to make the fabric water repellant. A common method for reducing linting of such fabrics is to treat the material with an external binder system. The nonwoven fabric is made water repellent by treatment with water proofing chemicals.

The External Binder System

While a wide variety of adhesives such as solid adhesives, hot melt adhesives, and adhesives dispersed in organic solvent can be applied as external binders to reduce linting, the preferred external binder system for reducing linting of a nonwoven fabric such as that of La Fitte is a latex binder applied as an aqueous emulsion into which the nonwoven fabric is immersed. The nonwoven fabric is then removed from the latex binder emulsion bath and dried before further processing. An alternative preferred method for applying the external binder system is to apply it as a concentrated emulsion by printing on the surface of the nonwoven fabric. Latex adhesives such as ethylene-vinylacetate latexes, acrylic latexes, styrene-butadiene rubber latexes, or other emulsifiable latex adhesives are preferred; especially preferred are ethylene vinylacetate latexes. Ethylenevinylacetate latex emulsions which are preferred have a nonionic surfactant, a latex solids content between 45 and 55 percent, a viscosity between 700 and 1200 cps (Brookfield viscosity with a #3 spindle, 60 rpm), and a pH between 5.0 and 6.0. Such latex emulsions are available commercially from Air Products & Chemicals, Inc., under the tradename Airflex.

The preferred concentration range for external binder latexes in aqueous emulsions to be applied to nonwoven fabrics is from about 1% to about 30%. For the fabric immersion process, the preferred latex concentration in the emulsion is between about 1% and about 5%; the preferred concentration range of the latex is from about 10% to about 30% for the printing process. The quantity of external binder added to the fabric is preferably from about 0.7 g/m$^2$ to about 4 g/m$^2$, from about 1 g/m$^2$ to about 2 g/m$^2$ is especially preferred.

The Monocarboxylate Antimicrobial Agent

The present invention utilizes monocarboxylates to impart antimicrobial activity to materials. Monocarboxylate antimicrobial agents include the nonaromatic $C_3$–$C_{12}$, inclusive, alkyl, alkenyl or alkynyl organic acids and their salts, and mixtures thereof. Such salts include, for example, sodium, potassium, ammonium, etc. salts. The water soluble acids and salts are preferred. The preferred monocarboxylate antimicrobial agents are the $C_6$–$C_{10}$ n-alkane monocarboxylates, especially preferred are the $C_8$ and $C_{10}$ n-alkane monocarboxylates. In their acid form, these monocarboxylates have a broad spectrum of kill for the types of bacteria and fungi most often found in hospitals, are safe to human and lower animals, and are compatible with the materials used herein.

The method for incorporating a monocarboxylate antimicrobial agent into a nonwoven fabric according to the present invention is to add the monocarboxylate to the external binder system. It has been found that when monocarboxylic acids are added to the preferred latex binder emulsion systems, that the acidic conditions tend to break the emulsion. Also, many of the monocarboxylic acids have an offensive odor that is imparted to the fabric if they are used. Therefore, a soluble monocarboxylate salt, rather than the acid, is added to the latex emulsion system. Sodium monocarboxylates are preferred for addition to the latex emulsion system.

The preferred concentration of the monocarboxylate in the external binder system will depend on the method of application, the quantity of external binder to be added to the fabric, the degree of antimicrobial activity desired, and the particular monocarboxylate utilized. The degree of effectiveness of the treatment is generally proportional to the quantity of monocarboxylate added to the fabric. Antimicrobial activity in fabric can be achieved by applying to the fabric a latex emulsion which contains from about 0.3% to about 40% monocarboxylate. For the immersion process, the preferred concentration of monocarboxylate in the latex emulsion is from about 1% to about 10%; for the printing process the preferred monocarboxylate concentration is from about 5% to about 40%. The deposition of monocarboxylates on the fabric is preferably from about 0.1 g/m$^2$ to about 20 g/m$^2$; more preferred is from about 2 g/m$^2$ to about 20 g/m$^2$ especially preferred is from about 5 g/m$^2$ to about 10 g/m$^2$.

The antimicrobial activity of the $C_3$–$C_{12}$ monocarboxylate antimicrobials used herein is directly related to the presence of their respective free acids. The concentration of free monocarboxylic acid, as opposed to the monocarboxylate salt (anionic) form is a function of pH. Accordingly, the amount of monocarboxylate salt which must be incorporated into the nonwoven fabric to obtain the desired antimicrobial activity will vary somewhat with the use pH.

Because of the greater antimicrobial activity of the monocarboxylates at lower pH, a proton donor substance is provided in the treated material which can create a low pH when the material is wetted. The present invention incorporates such a proton donor in a treatment step separate from that in which the monocarboxylate salt is added to the material to avoid premature interaction of the salt and the proton donor. For nonwoven fabric laminates such as those of LaFitte which are to be used for hospital or surgical purposes, the proton donor is added with the waterproofing treatment.

The Waterproofing Treatment

Any of a wide variety of waterproofing treatments can be utilized in the present invention. The preferred waterproofing treatments include aqueous emulsions of waxes, resins, silicone compounds, fluorochemical compounds, and mixtures thereof; especially preferred are aqueous emulsions containing a combination of a fluorochemical and a wax or resin extender.

Fluorochemicals used include straight chain, highly fluorinated hydrocarbons. Examples of preferred fluorochemical treatments include emulsions of fluorochemical polymers with a solids content of from about 20% to 45%. Such treatments are available commercially from E. I. Du Pont de Nemours, Inc. under the tradename ZONYL and from the 3M Company under the tradename SCOTCHBAN.

A preferred resin extender is a 100% solids waxy chip of triazine resin which is emulsified with hot water and an acid catalyst (pH about 2.2), having aluminum glycolate as its active ingredient. An antifoam agent is often included in such resin formulations; for example, silicone antifoam agents such as AF-72 available commercially from the General Electric Company.

Waxes used include paraffinic waxes, examples are available commercially from E. I. Du Pont de Nemours, Inc. The waxes are emulsified in water by the addition of a nonionic surfactant. Mixtures of waxes and resins may also be used as extenders.

The waterproofing chemicals are preferably incorporated in an aqueous emulsion at a concentration ranging from about 0.1% to about 7%. For the especially preferred combination of fluorochemical and extender, the preferred concentrations are from about 0.1% to about 0.5% fluorochemical, and from about 0.4% to about 1% extender. The quantity of waterproofing compounds deposited on the fabric are preferably from about 0.1 g/m$^2$ to about 2 g/m$^2$ fluorochemical and from about 0.2 g/m$^2$ to about 5 g/m$^2$ extender; especially preferred is about 0.2 g/m$^2$ to about 0.5 g/m$^2$ fluorochemical and from about 0.5 g/m$^2$ to about 1 g/m$^2$ extender.

The Proton Donor

The proton donors preferred for the present invention are Lowry-Bronsted acids which do not exhibit substantial antimicrobial activity at the concentrations employed herein. Such proton donor materials include, for example, citric acid (especially preferred), tartaric acid, malic acid, fumaric acid, maleic acid, malonic acid, ascorbic acid, barbituric acid, and mixtures thereof.

The concentration of the proton donor in the waterproofing treatment will depend on the method of application and the deposition of proton donor desired. The concentration of proton donor is preferably from about 0.1% to about 20%; especially preferred is from about 1% to about 10%. The deposition of proton donor on the fabric is preferably from about 0.1 g/m$^2$ to about 20 g/m$^2$; more preferred is from about 1 g/m$^2$ to about 20 g/m$^2$; especially preferred is a deposition of from about 3 g/m$^2$ to about 10 g/m$^2$.

The waterproofing treatment containing the proton donor is preferably applied to nonwoven fabric to which an external binder system containing a monocarboxylate salt has previously been applied. Such nonwoven fabric is preferably immersed in the waterproofing treatment, quickly removed, and dried. During such an application of the waterproofing treatment, some of the monocarboxylate salt undoubtedly becomes dissolved in the acidic system resulting in formation of the corresponding monocarboxylic acid. The immersion in, removal from, and drying of the waterproofing treatment is done quickly to minimize such formation of monocarboxylic acid in the nonwoven fabric. The primary purpose for minimizing monocarboxylic acid formation is to avoid the resulting unpleasant odor.

While it is not intended to limit the scope of the present invention to a particular mechanism of action, it is believed that a nonwoven fabric treated as described previously acts as a positive barrier to the transmission or growth of bacteria, fungi, and mold in or through the material in the following manner. For microbial transport or growth to occur, the nonwoven fabric must be wetted. When the nonwoven fabric is wetted, the proton donor substance creates a low pH environment in which the monocarboxylate salt is converted to the corresponding monocarboxylic acid. The monocarboxylic acid is the active antimicrobial which prevents microbial transport through or microbial growth on the nonwoven fabric.

The ability of the treated nonwoven fabric to achieve the needed low pH condition when wetted can be determined by moistening the material with distilled water and measuring its pH with a Corning Flat-Surface Combination pH Electrode. The preferred surface pH of the treated materials of the present invention is from about 2.8 to about 5.0; especially preferred is from about 3.0 to about 4.0.

In order to predict the relative effectiveness of the treated material of this invention in preventing bacterial transport through the material, the following tests were developed:

Test Procedure-Bacteria Pressure Strikethrough

1. Wear sterile gloves throughout the test.
2. Cut material samples into 4"×4" squares. Place them under ultraviolet light for one hour on each side to sterilize.
3. Cut two 6"×6" squares for each sample from autoclavable poly bags. Sterilize in the autoclave.
4. Clean press, elevating block and plexiglass plates with an antimicrobial detergent. Be sure all surfaces are completely dry before testing.
5. Prepare a solution of Staphylococcus epidermis of about 10$^6$ bacterial count per 1 ml of the solution to be used in testing. Determine the actual bacterial count of this solution.
6. Place a plexiglass plate on the elevating block which is centered beneath the press. The purpose of this block is to raise the sample to the level required by the press. Using sterile forceps, take one piece of sterile poly film and place it on the plate followed by a test sample. Put 0.1 ml of the bacteria solution on the center of the sample. Cover the sample with another piece of sterile film, followed by the other plexiglass plate and then the steel block. Submit this sandwich to a large pressure, sufficient to guarantee strikethrough, for 10 seconds. Remove the steel block and the top plexiglass plate. Place the test sample and both pieces of poly film in a stomacher bag or blender, separating the test sample and pieces of film as this is done.

Pour 100 ml of sterile water into the bag or blender. Digest in the stomacher bag or blend for 30 seconds. Plate the liquid elutions at appropriate dilutions. Incubate plates for 48 hours.

Test Procedure-Time Release Test

This test is a modification of the Bacteria Pressure Strikethrough Test. The procedures for strikethrough and plating are the same.

The number of samples required to run a time release test include one sample for every hour of testing, plus two additional—one as a control and one for the initial strikethrough. The control is placed directly in the stomacher or blender without being submitted to a strikethrough along with two pieces of poly film. All of the remaining samples are struck through initially and every hour thereafter with 1 sample being taken each hour for analysis. Those samples remaining at any time are placed under a sterile hood between strikethroughs.

EXAMPLES 1-9

A three-ply nonwoven fabric laminate consisting of two plies of tissue laminated on either side of a nylon spunbonded web was made according to the teachings of LaFitte such that the resulting nonwoven fabric had a basis weight of about 90 g/m$^2$. The nonwoven fabric was immersion treated by an external latex binder system which was an aqueous ethylene-vinylacetate latex emulsion containing 4% latex solids and 10% sodium octanoate. The nonwoven fabric was dried and then treated in a waterproofing saturation bath. The waterproofing treatment was an aqueous emulsion containing 0.5% fluorochemical polymers, 1.0% paraffinic waxes, and 10% citric acid. The nonwoven fabric was again dried. Although the uptake of the chemicals was not measured for these particular samples, historical data experience indicates that uptake of the latex emulsion and waterproofing emulsion was about 100% and 90% (dry fabric basis), respectively.

Eleven samples of the nonwoven fabric thus treated were prepared for a nine hour Time Release Test as described above. Results of the test are shown in the following table:

| Example No. | Time (hr.) | Total Bacteria Added | Total Bacteria Remaining | Logs Reduced | Percent Kill |
|---|---|---|---|---|---|
| 1 | 0 | 3.3 × 10$^5$ | 0 | 5 | 99.999% |
| 2 | 1 | 6.6 × 10$^5$ | 3.1 × 10$^2$ | 3 | 99.953% |
| 3 | 2 | 9.9 × 10$^5$ | 5.2 × 10$^2$ | 3 | 99.947% |
| 4 | 3 | 1.32 × 10$^6$ | 2.0 × 10$^2$ | 4 | 99.984% |
| 5 | 4 | 1.65 × 10$^6$ | 7.7 × 10$^2$ | 4 | 99.953% |
| 6 | 5 | 1.86 × 10$^6$ | 3.5 × 10$^2$ | 4 | 99.981% |
| 7 | 6 | 1.39 × 10$^7$ | 4.4 × 10$^4$ | 3 | 99.682% |
| 8 | 7 | 1.41 × 10$^7$ | 1.0 × 10$^2$ | 5 | 99.999% |
| 9 | 8 | 1.43 × 10$^7$ | 0 | 7 | 99.999% |

Examples 1-9 show that the present invention provides for production of nonwoven fabric which is effective in substantially reducing the number of bacteria which come in contact with it even when it is repeatedly subjected to sequential bacterial contamination.

EXAMPLES 10-12

A three-ply nonwoven fabric laminate consisting of two plies of tissue laminated on either side of a nylon spunbonded web was made according to the teachings of LaFitte such that the resulting nonwoven fabric had a basis weight of about 90 g/m$^2$. The nonwoven fabric was gravure printed with an external latex binder system which was an aqueous ethylene-vinylacetate latex emulsion containing 12% latex solids. The nonwoven fabric was dried and then treated in a waterproofing saturation bath. The waterproofing treatment was an aqueous emulsion containing 0.5% fluorochemical polymers and 1.0% triazine resins and aluminum glycolate catalyst. The nonwoven fabric was again dried.

For Example 10, the waterproofing bath also contained 5.0% citric acid, but there was no monocarboxylate added to the external binder system. For Example 11, the external binder system also contained 36% sodium octanoate, but there was no citric acid added to the waterproofing bath. For Example 12, the external latex binder system contained 36% sodium octanoate and the waterproofing bath contained 5% citric acid. For Examples 11 and 12, the addition of sodium octanoate with the external binder system resulted in a deposition of about 2 g/m$^2$ sodium octanoate to the nonwoven fabrics. For Examples 10 and 12, the resulting deposition of citric acid to the nonwoven fabrics was about 4.5 g/m$^2$.

The following test procedure was used to evaluate Examples 10-12. Using 4"×4" pieces of the nonwoven fabric to be tested, the nonwoven fabric is inoculated with 0.1 ml. of a 24-hour culture of E. coli that has a known count. After inoculating, the nonwoven fabric is sandwiched between sterile pieces of plastic and pressed to 167 psi for 30 seconds to assure absorption of the liquid inoculum by the nonwoven fabric. The inoculated nonwoven fabric is taken out of the press and allowed to react until a predetermined contact time has elapsed; at which time the inoculated nonwoven fabric is placed into 100 ml. of neutralizer to stop the bactericidal affect of the treated nonwoven fabric. The neutralizer and nonwoven fabric are blended for 60 seconds. 1.0 ml. of the neutralizer is plated. Plates are incubated for 48 hours and colonies of bacteria are counted.

The following table shows the results of the test evaluation for antibacterial properties of the nonwoven fabrics of Examples 10-22:

| Example No. | Total Bacteria Added | Contact Time (min.) | Percent Kill |
|---|---|---|---|
| 10 | 9.5 × 10$^4$ | 10 | 56.93% |
| 10 | 9.5 × 10$^4$ | 12 | 83.92% |
| 11 | 1.2 × 10$^5$ | 10 | 31.38% |
| 11 | 1.2 × 10$^5$ | 12 | 49.12% |
| 12 | 9.1 × 10$^5$ | 10 | 90.77% |
| 12 | 9.1 × 10$^5$ | 12 | 96.67% |

Examples 10-12 demonstrate the effective antibacterial action achieved by the addition of antibacterial agent to a nonwoven fabric according to the present invention.

While particular embodiments of the present invention have been illustrated and described, it would be obvious to those skilled in the art that various changes and modifications can be made without departing from the spirit and scope of the invention. It is intended to cover, in the appended claims, all such modifications that are within the scope of the invention.

What is claimed is:

1. A process for imparting antimicrobial properties to a material, said process comprising:
    (a) applying an external binder system to said material, said external binder system comprising a salt of at least one monocarboxylate antimicrobial agent or mixtures thereof;
    (b) applying a waterproofing treatment to said material, said treatment comprising at least one substantially nonantimicrobial proton donor; and
    (c) drying said material.

2. The process of claim 1 wherein said material is a nonwoven fabric comprising cellulosic fibers.

3. The process of claim 1 wherein said monocarboxylate antimicrobial agent comprises a $C_3$-$C_{12}$ alkane, alkene, or alkyne monocarboxylate.

4. The process of claim 2 wherein said monocarboxylate antimicrobial agent comprises a $C_6$–$C_{10}$ n-alkane monocarboxylate.

5. The process of claim 2 wherein said monocarboxylate antimicrobial agent comprises a $C_8$ or $C_{10}$ n-alkane monocarboxylate.

6. The process of claim 3 wherein said waterproofing treatment is an aqueous emulsion and said substantially nonantimicrobial proton donor is an acid selected from the group of citric acid, tartaric acid, malic acid, fumaric acid, maleic acid, malonic acid, ascorbic acid, barbituric acid, and mixtures thereof.

7. The process of claim 4 wherein said waterproofing treatment is an aqueous emulsion and said substantially nonantimicrobial proton donor is an acid selected from the group of citric acid, tartaric acid, malic acid, fumaric acid, maleic acid, malonic acid, ascorbic acid, barbituric acid, and mixtures thereof.

8. The nonwoven fabric made according to claim 7.

9. The process of claim 5 wherein said waterproofing treatment is an aqueous emulsion and said substantially nonantimicrobial proton donor is citric acid.

10. The nonwoven fabric made according to claim 9.

11. The process of claim 3 wherein said external binder system is an aqueous latex emulsion applied such that a deposition of from about 0.1 g/m² to about 20 g/m² of said antimicrobial agent is provided on said material, said material is dried prior to said application of waterproofing treatment, and said waterproofing treatment application provides a deposition of from about 0.1 g/m² to about 20 g/m² of said proton donor on said material.

12. The process of claim 6 wherein said external binder system is an aqueous latex emulsion applied such that a deposition of from about 0.1 g/m² to about 20 g/m² of said antimicrobial agent is provided on said material, said material is dried prior to said application of waterproofing treatment, and said waterproofing treatment application provides a deposition of from about 0.1 g/m² to about 20 g/m² of said proton donor on said material.

13. The process of claim 4 wherein said external binder system is an aqueous latex emulsion, applied such that a deposition of from about 2 g/m² to about 20 g/m² of said antimicrobial agent is provided on said nonwoven fabric, said nonwoven fabric is dried prior to said application of waterproofing treatment and said waterproofing treatment application provides a deposition of from about 1 g/m² to about 20 g/m² of said proton donor to said nonwoven fabric such that the surface pH of said nonwoven fabric when wetted after step (c) is from about 2.8 to about 5.0.

14. The process of claim 7 wherein said external binder system is an aqueous latex emulsion, applied such that a deposition of from about 2 g/m² to about 20 g/m² of said antimicrobial agent is provided on said nonwoven fabric, said nonwoven fabric is dried prior to said application of waterproofing treatment and said waterproofing treatment application provides a deposition of from about 1 g/m² to about 20 g/m² of said proton donor to said nonwoven fabric such that the surface pH of said nonwoven fabric when wetted after step (c) is from about 2.8 to about 5.0.

15. The nonwoven fabric made according to claim 14.

16. The process of claim 5 wherein said external binder system is an aqueous latex emulsion, applied such that a deposition of from about 5 g/m² to about 10 g/m² of said antimicrobial agent is provided on said nonwoven fabric, said nonwoven fabric is dried prior to said application of waterproofing treatment, said waterproofing treatment is an aqueous emulsion, said substantially nonantimicrobial proton donor is citric acid, and said waterproofing treatment application provides a deposition of from about 3 g/m² to about 10 g/m² of said proton donor to said nonwoven fabric such that the surface pH of said nonwoven fabric when wetted after step (c) is from about 3.0 to about 4.0.

17. The nonwoven fabric made according to claim 16.

* * * * *